United States Patent
Jung et al.

[11] Patent Number: 6,087,521
[45] Date of Patent: Jul. 11, 2000

[54] SILICON COMPOUNDS CONTAINING SILAMETHYLENE BONDS AND METHOD FOR THEIR PREPARATION

[76] Inventors: Il Nam Jung, 21-1303 Hyundai Apt., Ogum-dong, Songpa-ku, Seoul 138-130; Bok Ryul Yoo, 903-303 Lotte Apt., 1058 Ilsan-3-dong, Ilsan-ku, Koyang-si, Kyunggi, 411-313; Joon Soo Han, 801-2401 Hyndai Apt., Kwangjang-dong, Kwangjinku, Seoul 138-130; Weon Cheol Lim, 1-906 Dongin Apt., Kaebong-dong, Kuro-ku, Seoul 152-092, all of Rep. of Korea

[21] Appl. No.: 09/312,899

[22] Filed: May 17, 1999

[51] Int. Cl.[7] .................................................. C07F 7/08
[52] U.S. Cl. ................................................................. 556/435
[58] Field of Search ............................................... 556/435

[56] References Cited

U.S. PATENT DOCUMENTS

| | | | |
|---|---|---|---|
| 3,159,601 | 12/1964 | Ashby | 260/46.5 |
| 3,220,972 | 11/1965 | Lamoreaux | 260/46.5 |
| 3,296,291 | 1/1967 | Chalk et al. | 260/448.2 |
| 3,419,593 | 12/1968 | Willing | 260/448.2 |
| 3,516,946 | 6/1970 | Modic | 252/429 |
| 3,814,730 | 6/1974 | Karstedt | 260/46.5 |
| 3,928,629 | 12/1975 | Chandra et al. | 427/387 |
| 3,989,668 | 11/1976 | Lee et al. | 260/46.5 |
| 5,036,117 | 7/1991 | Chang et al. | 522/172 |
| 5,235,083 | 8/1993 | Jung et al. | 556/435 |
| 5,332,849 | 7/1994 | Jung et al. | 556/435 |
| 5,391,794 | 2/1995 | Jung et al. | 556/435 |
| 5,399,740 | 3/1995 | Jung et al. | 556/435 |
| 5,420,323 | 5/1995 | Jung et al. | 556/435 |
| 5,527,934 | 6/1996 | Jung et al. | 556/435 |
| 5,998,649 | 12/1999 | Jung et al. | 556/435 |

OTHER PUBLICATIONS

Yeon et al., "Effects of Hydrogen Chloride Addition to the Direct Reaction of Methylene Chloride with Elemental Silicon," J. Organomet. Chem. 1996, 516, 91.

Han et al., "Direct Synthesis of Tris(chlorosilyl)methanes Containing Si–H Bonds," Organometallics. 1997, 16, 93.

Speier et al., "The Addition of Silicon Hydrides to Olefinic Double Bonds. Part II. The Use of Group VIII Metal Catalysts," J. Am. Chem. Soc., 1957, 79,974.

*Primary Examiner*—Paul F. Shaver
*Attorney, Agent, or Firm*—William F. Boley

[57] ABSTRACT

The present invention is organosilicon compounds described by formula (1)

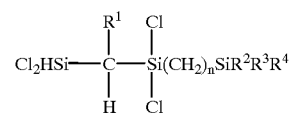

and formula (2)

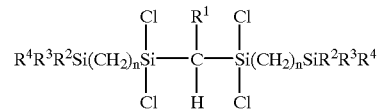

were $R^1$ is selected from the group consisting of hydrogen, dichlorosilyl, trichlorosilyl, methyldichlorosilyl, dimethylchlorosilyl, and trimethylsilyl, each $R^2$, $R^3$, and $R^4$ are independently selected from the group consisting of hydrogen, chlorine, alkoxy radicals comprising 1 to about 12 carbon atoms, aryloxy radicals comprising up to about 12 carbon atoms, aryl radicals comprising up to about 12 carbon atoms, and saturated hydrocarbon radicals comprising 1 to about 12 carbon atoms, and n=2 to 6; and methods for the making of organosilicon compounds described by formulas (1) and (2).

15 Claims, No Drawings

SILICON COMPOUNDS CONTAINING SILAMETHYLENE BONDS AND METHOD FOR THEIR PREPARATION

BACKGROUND OF INVENTION

The present invention is novel organosilicon compounds having silamethylene bonds and methods for their preparation by a hydrosilation reaction. Since the description of hexachloroplatinic acid as a catalyst for hydrosilation in 1957 by Speier et al., hydrosilation has become one of the fundamental methods for synthesizing organosilicon compounds. Speier et al., *J. Am. Chem. Soc.* 1957, 79, 974. In the hydrosilation process Si—H bond containing silicon compounds are reacted and added to multiple bonds of organic compounds such as carbon-carbon, carbon-oxygen, carbonnitrogen, nitrogen-nitrogen, and nitrogen oxygen.

Yeon et al., *J. Organomet. Chem.* 1996, 516, 91, reported in 1996 the direct synthesis of Si—H containing bis(silyl) methanes by reacting silicon metal with a mixture of methylene chloride and hydrogen chloride.

Jung et al., U.S. Pat. No. 5,399,740, describe the reaction of silicon metal with a mixture of dichloromethyl group containing silane and hydrogen chloride to obtain tris(silyl) methanes in moderately high yield.

Han et al., Organometallics 1997, 16, 93, reported the direct synthesis of Si—H containing tris(silyl)methanes by reacting silicon metal with a mixture of chloroform and hydrogen chloride.

The organosilicon compounds of the present invention are useful, for example, as intermediates for forming silicon carbides by pyrolysis.

SUMMARY OF INVENTION

The present invention is organosilicon compounds described by formula (1)

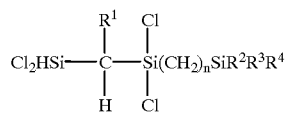

and formula (2)

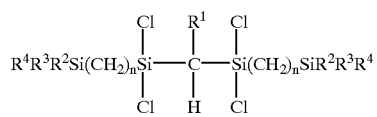

where $R^1$ is selected from the group consisting of hydrogen, dichlorosilyl, trichlorosilyl, methyldichlorosilyl, dimethylchlorosilyl, and trimethylsilyl, each $R^2$, $R^3$, and $R^4$ are independently selected from the group consisting of hydrogen, chlorine, alkoxy radicals comprising 1 to about 12 carbon atoms, aryloxy radicals comprising up to about 12 carbon atoms, aryl radicals comprising up to about 12 carbon atoms, and saturated hydrocarbon radicals comprising 1 to about 12 carbon atoms, and n=2 to 6; and methods for the making of organosilicon compounds described by formulas (1) and (2).

DESCRIPTION OF INVENTION

The present invention is organosilicon compounds described by formula (1)

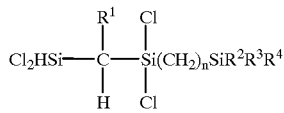

and formula (2)

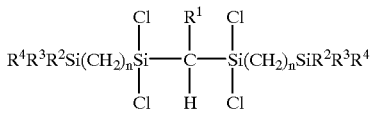

were $R^1$ is selected from the group consisting of hydrogen, dichlorosilyl, trichlorosilyl, methyldichlorosilyl, dimethylchlorosilyl, and trimethylsilyl, each $R^2$, $R^3$, and $R^4$ are independently selected from the group consisting of hydrogen, chlorine, alkoxy radicals comprising 1 to about 12 carbon atoms, aryloxy radicals comprising up to about 12 carbon atoms, aryl radicals comprising up to about 12 carbon atoms, and saturated hydrocarbon radicals comprising 1 to about 12 carbon atoms, and n=2 to 6; and methods for the making of organosilicon compounds described by formulas (1) and (2).

In formulas (1) and (2) each $R^2$, $R^3$, and $R^4$ can be, for example hydrogen, chlorine, methoxy, ethoxy, phenoxy, methyl, ethyl, tert-butyl, cyclopentyl, cyclohexyl, phenyl, chlorophenyl, and chloromethyl. In formulas (1) and (2) it is preferred that each $R^2$, $R^3$, and $R^4$ be independently selected from the group consisting of hydrogen, chlorine, and methyl.

In formulas (1) and (2), n=2 to 6 and in formula (2) each n can be the same or different value. Preferred is where in formulas (1) and (2), n=2 or 3 and in formula (2) each n is the same value.

Preferred organosilicon compounds within the scope of formulas (1) and (2) are selected from the group consisting of 1,1,3,3,6,6-hexachloro-1,3,6-trisilaheptane; 2,2,5,5,7,7,10,10-octachloro-2,5,7,10-tetrasilaundecane; 1,1,1,4,4,6,6-heptachloro-1,4,6-trisilahexane; 1,1,1,4,4,6,6,9,9,9-decachloro-1,4,6,9-tetrasilanonane; 1,1,1,3,3,6,6-heptachloro-2-dichlorosilyl-1,3,6-trisilaheptane; 1,1,1,3,3,6,6,6-octachloro-2-dichlorosilyl-1,3,6-trisilahexane; 2,2,4,4,7,7-hexachloro-3-dichlorosilyl-2,4,7-trisilaoctane; and 2,2,4,4,7,7,7-heptachloro-3-dichlorosilyl-2,4,7-trisilaheptane.

The present invention is also a method for making organosilicon compounds described by formulas (1) and (2). The method comprises effecting hydrosilation of a bis (dichlorosilyl)methane described by formula (3)

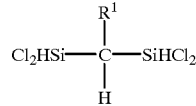

with an unsaturated organosilane described by formula (4)

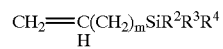

in the presence of an effective amount of hydrosilation catalyst, where $R^1$, $R^2$, $R^3$, and $R^4$ are as previously described and m=0 to 4. In a preferred method m=0.

Preferred examples of the bis(dichlorosilyl)methane include bis(dichlorosilyl)methane, bis(dichlorosilyl)

trichlorosilylmethane, and bis(dichlorosilyl) dichloromethylsilylmethane.

Preferred examples of the unsaturated organosilane include dichloromethylvinylsilane and trichlorovinylsilane.

The mole ratio of the unsaturated organosilane to the bis(dichlorosilyl)methane added to the method can be within a range of about 0.1 to 10. It is preferred that the mole ratio of the unsaturated organosilane to the bis(dichlorosilyl) methane be within a range of about 0.5 to 2. It is preferred that he mole ratio of unsaturated organosilane to the bis (dichlorosilyl)methane be within a range of about 0.5 to 1.5 when the desired product is described by formula (1) and within a range of about 0.75 to 2 when the desired product is described by formula 2.

The present method requires the presence of an effective amount of a metallic hydrosilation catalyst. The metallic hydrosilation catalyst can be any such catalyst which is known to catalyze the reaction of silicon-bonded hydrogen atoms with silicon-bonded alkenyl groups. The preferred metallic hydrosilation catalyst for use in the present method are platinum group metal-containing catalyst. By "platinum group metal" it is meant ruthenium, rhodium, palladium, osmium, iridium, and platinum. Examples of platinum group metal-containing catalyst which may be useful in the present method are found in, for example, Willing, U.S. Pat. No. 3,419,593; Lee et al., U.S. Pat. No. 3,989,668; Chang et al., U.S. Pat. No. 5,036,117; Ashby, U.S. Pat. No. 3,159,601; Lamoreaux, U.S. Pat. No. 3,220,972; Chalk et al., U.S. Pat. No. 3,296,291; Modic, U.S. Pat. No. 3,516,946; Karstedt, U.S. Pat. No. 3,814,730; and Chandra et al., U.S. Pat. No. 3,928,629 all of which are hereby incorporated by reference to show useful platinum group metal-containing catalyst and methods for their preparation. A preferred platinum group metal is platinum. The preferred platinum group metal catalysts are compounds and complexes of platinum. Examples of metallic hydrosilation catalysts which may be useful in the present method include $H_2PtCl_6$, $H_2PtCl_6$ in solution in isopropyl alcohol (IPA), $H_2PtCl_6$/IPA/$PPh_3$ solutions, $Pt(PPh_3)_4$, $Pt(CH_2=CH_2)(PPh_3)_2$, $RhCl(PPh_3)_3$, $Pd(PPh_3)_4$, and $Ni(PEt_3)_4$; where Et is ethyl and Ph is phenyl. The preferred catalyst for use in the present invention is an isopropyl alcohol solution of $H_2PtCl_6$.

The present method requires that an effective amount of a metallic hydrosilation catalyst be added. By the term "effective amount" it is meant an amount of catalyst sufficient to accelerate a reaction between the silicon-bonded hydrogen atoms of the bis(dichlorosilyl)methane and the unsaturated organosilane. Generally, an effective amount of the metallic hydrosilation catalyst is an amount with a range of about $1\times10^{-5}$ to 0.05 moles of metal per mole of the bis(dichlorosilyl)methane added to the method.

The method of effecting hydrosilation of the bis (dichlorosilyl)methane with the unsaturated organosilane can be any of those known methods for effecting hydrosilation reactions in the presence of a metallic hydrosilation catalyst. In a preferred process an optional organic solvent, the bis(dichlorosilyl)methane, and the metallic hydrosilation catalyst are placed in a reactor under an inert atmosphere such as dried nitrogen. The unsaturated organosilane is then slowly added to the reactor with stirring. After addition of the unsaturated organosilane, the reactor content may be further heated at a temperature from about 10° C. to 150° C. for a time sufficient to ensure completion of the hydrosilation reaction. It is preferred to heat the reactor content at a temperature within a range of about 20° C. to 150° C., and even more preferred is a temperature of about 25° C. to 110° C. The length of time the reactor content is heated to effect the hydrosilation reaction will depended upon the reactants and the temperature to which the reactor content is heated. Generally a time of about 0.5 hours to 20 hours is useful, with a a heating time of about 1 hour to 5 hours being preferred.

The use of an organic solvent in the present method is optional. Organic solvents which may be useful in the present method include benzene, toluene, xylene, chlorobenzene, and anisole. The organic solvent may be added to the method as a diluent in any amount that preferably does not dilute the reactants to a point that detrimentally effects the reaction rate and yield.

The following examples are provided to illustrate the present invention. These examples are not intended to limit the scope of the claims herein.

EXAMPLE 1

Hydrosilation of dichloromethylvinylsilane with bis (dichlorosilyl)methane. To a 250 ml flame dried flask equipped with a magnetic stirrer and reflux condenser was added 85 g of bis(dichlorosilyl)methane and 200 μl of 0.1 M $H_2PtCl_6$/IPA solution and the flask placed under a dry nitrogen atmosphere. Then, to the flask was added 42.1 g of dichloromethylvinylsilane and the flask content stirred for 40 minutes. The temperature of the flask content was then increased to 90° C. and stirring continued for 2 hours. The flask content was vacuum distilled at 67 Pa to yield 91.8 g of 1,1,3,3,6,6-hexachloro-1,3,6-trisilaheptane; $^1$H-NMR ($CDCl_3$, ppm): 0.85 (s,3H, $SiCH_3$), 1.23–1.48 (m, 6H, $SiCH_2SiCH_2CH_2Si$), 5.71 (s, 1H, SiH). The distillation residue was recrystallized with hexane to give 16.2 g of 2,2,5,5,7,7,10,10-octachloro-2,5,7,10-tetrasilaundecane as colorless needle-type crystals; $^1$H-NMR ($CDCl_3$, ppm): 0.81–0.84 (s, 6H, $SiCH_3$), 1.23–1.38 (m, 10H, $SiCH_2CH_2SiCH_2Si$).

EXAMPLE 2

Hydrosilation of trichlorovinylsilane with bis(dichlorosilyl) methane. In the same apparatus as described in Example 1, 3.3 g of bis(dichlorosilyl)methane, 20 ml of dried benzene, and 60 μl of 0.1 M $H_2PtCl_6$/IPA solution were placed and the flask placed under a dry nitrogen atmosphere. Then, to the flask were added 1.2 g of trichlorovinylsilane and the flask content stirred for 5 minutes. The flask content was refluxed with stirring for 2 hours. Then, the flask content was vacuum distilled at 67 Pa to give 3.4 g of a mixture comprising 1,1,1,4,4,6,6-heptachloro-1,4,6-trisilahexane (TCD-GC area of 69.7%)(TCD-GC=thermal conductivity detection-gas chromotography) and 1,1,1,4,4,6,6,9,9,9-decachloro-1,4,6, 9-tetrasilanonane (TCD-GC area 3.7%). 1,1,1,4,4,6,6-Heptachloro-1,4,6-trisilahexane: $^1$H-NMR ($CDCl_3$, ppm): 1.35–1.57 (m, 6H, $SiCH_2SiCH_2CH_2Si$) 5.71 (s, 1H, SiH). 1,1,1,4,4,6,6,9,9,9-Decachloro-1,4,6,9-tetrasilanonane: $^1$H-NMR ($CDCl_3$, ppm): 1.26–1.53(m, 10H, $CH_2CH_2SiCH_2SiCH_2CH_2$).

EXAMPLE 3

Hydrosilation of dichloromethylvinylsilane with bis (dichlorosilyl)trichlorosilylmethane. In the same apparatus as described in Example 1, 2.5 g of bis(dichlorosilyl) trichlorosilylmethane, 20 ml of dried benzene, and 40 μl of 0.1 M $H_2PtCl_6$/IPA solution were placed. Then, to the flask was added 0.5 g of dichloromethylvinylsilane and the flask content stirred for 5 minutes. The flask content was refluxed with stirring for 2 hours. Then, the flask content was vacuum distilled at 67 Pa to give 1.7 g of a mixture comprising 1,1,1,3,3,6,6-heptachloro-2-dichlorosilyl-1,3,6-trisilaheptane (TCD-GC area 75.1%); $^1$H-NMR ($CDCl_3$, ppm): 0.84 (s, 3H, SiCH$_3$), 1.27–1.33, 1.46–1.56 (m, 4H, SiCH$_2$CH$_2$Si), 1.85 (s, 1H, SiCH) 5.89 (s, 1H, SiH).

EXAMPLE 4

Hydrosilation of trichlorovinylsilane with bis(dichlorosilyl) trichlorosilylmethane. In the same apparatus as described in Example 1, 2.5 g of bis(dichlorosilyl)trichlorosilylmethane, 20 ml of dried benzene, and 50 μl of 0.1 M H$_2$PtCl$_6$/IPA solution where placed. Then, to the flask was added 0.58 g of dichloromethylvinylsilane and the flask content stirred for 5 minutes. The flask content was refluxed with stirring for 2 hours. Then, the flask content was vacuum distilled at 67 Pa to give 1.75 g 1,1,1,3,3,6,6,6-octachloro-2-dichlorosilyl-1, 3,6-trisilahexane (TCD-GC area 71.9%) as a mixture. $^1$H-NMR (CDCl$_3$, ppm): 1.53–1.59 (m, 4H, SiCH$_2$CH$_2$Si), 1.86 (s, 1H, SiCH), 5.89 (s, 1H, SiH).

EXAMPLE 5

Hydrosilation of dichloromethylvinylsilane with bis (dichlorosilyl)dichloromethylsilylmethane. In the same apparatus as described in Example 1, 10 g of bis (dichlorosilyl)dichloromethylsilylmethane, 30 ml of dried benzene, and 80 μl of 0.1 M H$_2$PtCl$_6$/IPA solution were placed. Then, to the flask were added 4 ml of dichloromethylvinylsilane and the flask content stirred for 15 minutes. The flask content was refluxed with stirring for 1 hour. Then, the flask content was vacuum distilled at 67 Pa to give 14.7 g of 2,2,4,4,7,7-hexachloro-3-dichlorosilyl-2,4,7-trisilaoctane(TCD-GC area 95.3%) as a mixture. $^1$H-NMR (CDCl$_3$, ppm): 0.84 (s, 3H, CH$_2$SiCH$_3$), 1.13 (s, 3H, CHSiCH$_3$), 1.33–1.58 (m, 5H, CHSiCH$_2$CH$_2$Si) 5.89 (s, 1H, SiH).

EXAMPLE 6

Hydrosilation of trichlorovinylsilane with bis(dichlorosilyl) dichloromethylsilylmethane. In the same apparatus as described in Example 1, 10 g of bis(dichlorosilyl) dichloromethylsilylmethane, 30 ml of dried benzene, and 80 μl of 0.1 M H$_2$PtCl$_6$/IPA solution were placed. Then, to the flask were added 3.89 ml of trichlorovinylsilane and the flask content stirred for 15 minutes. The flask content was refluxed with stirring for 2 hours. Then, the flask content was vacuum distilled at 67 Pa to give 15.2 g of 2,2,4,4,7,7,7-heptachloro-3-dichlorosilyl-2,4,7-trisilaheptane (TCD-GC area 94.5%) as a mixture. 1H-NMR (CDCl$_3$, ppm): 1.14 (s, 3H, CHSiCH$_3$), 1.56–1.60 (m, 5H, CHSiCH$_2$CH$_2$Si), 5.89 (s, 1H, SiH).

We claim:

1. An organosilicon compound containing a silamethylene bond described by formula

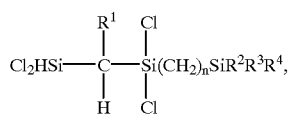

were R$^1$ is selected from the group consisting of hydrogen, dichlorosilyl, trichlorosilyl, methyldichlorosilyl, dimethylchlorosilyl, and trimethylsilyl, each R$^2$, R$^3$, and R$^4$ are independently selected from the group consisting of hydrogen, chlorine, alkoxy radicals comprising 1 to about 12 carbon atoms, aryloxy radicals comprising up to about 12 carbon atoms, aryl radicals comprising up to about 12 carbon atoms, and saturated hydrocarbon radicals comprising 1 to about 12 carbon atoms, and n=2 to 6.

2. An organosilicon compound containing a silamethylene bond described by formula

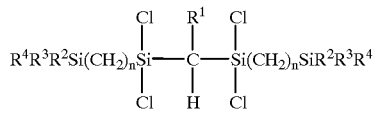

were R$^1$ is selected from the group consisting of hydrogen, dichlorosilyl, trichlorosilyl, methyldichlorosilyl, dimethylchlorosilyl, and trimethylsilyl, each R$^2$, R$^3$, and R$^4$ are independently selected from the group consisting of hydrogen, chlorine, alkoxy radicals comprising 1 to about 12 carbon atoms, aryloxy radicals comprising up to about 12 carbon atoms, aryl radicals comprising up to about 12 carbon atoms, and saturated hydrocarbon radicals comprising 1 to about 12 carbon atoms, and n=2 to 6.

3. An organosilicon compound according to claim 1, where R$^2$, R$^3$, and R$^4$ are independently selected from the group consisting of hydrogen, chlorine, and methyl.

4. An organosilicon compound according to claim 2, where R$^2$, R$^3$, and R$^4$ are independently selected from the group consisting of hydrogen, chlorine, and methyl.

5. An organosilicon compound according to claim 1, where n=2 or 3.

6. An organosilicon compound according to claim 1, where n=2 or 3 and each n is the same value.

7. A method for making organosilicon compounds described by formula

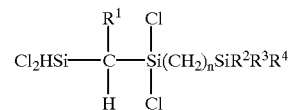

and

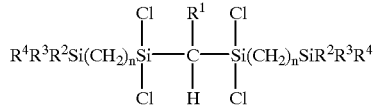

comprising effecting hydrosilation of a bis(dichlorosilyl) methane described by formula

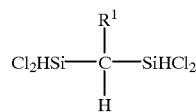

with an unsaturated organosilane described by formula

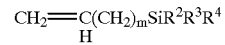

in the presence of an effective amount of metallic hydrosilation catalyst, where R$^1$ is selected from the group consisting of hydrogen, dichlorosilyl, trichlorosilyl, methyldichlorosilyl, dimethylchlorosilyl, and trimethylsilyl, each R$^2$, R$^3$, and R$^4$ are independently selected from the group consisting of hydrogen, chlorine, alkoxy radicals comprising 1 to about 12 carbon atoms, aryloxy radicals comprising up to about 12 carbon atoms, aryl radicals comprising up to about 12 carbon atoms, and saturated hydrocarbon radicals comprising 1 to about 12 carbon atoms, and m=0 to 4.

8. A method according to claim 7, where $R^2$, $R^3$, and $R^4$ are independently selected from the group consisting of hydrogen, chlorine, and methyl.

9. A method according to claim 7, where the bis(dichlorosilyl)methane is selected from the group consisting of bis(dichlorosilyl)methane, bis(dichlorosilyl)trichlorosilylmethane, and bis(dichlorosilyl)dichloromethylsilylmethane.

10. A method according to claim 7, where the unsaturated organosilane is selected from the group consisting of dichloromethylvinylsilane and trichlorovinylsilane.

11. A method according to claim 7, where the mole ratio of the unsaturated organosilane to the bis(dichlorosilyl)methane is within a range of about 0.5 to 1.5.

12. A method according to claim 7, where the mole ratio of the unsaturated organosilane to the bis(dichlorosilyl)methane is within a range of about 0.75 to 2.

13. A method according to claim 7, where the metallic hydrosilation catalyst is selected from the group consisting of $H_2PtCl_6$, $H_2PtCl_6/IPA$, $H_2PtCl_6/PPh_3$, $H_2PtCl_6/THF$, $H_2PtCl_6/I_2$, $Pt((CH_2=CHSiMe_2)_2O)_2$, $Pt(CH_2=CH)(PPh_3)_2$, $Pt(PPh_3)_4$, $Ni(PEt_3)_4$, $RhCl(PPh_3)_3$, and $Pd(PPh_3)_4$.

14. A method according to claim 7, where the metallic hydrosilation catalyst is $H_2PtCl_6/IPA$.

15. A method according to claim 7 further comprising the presence of an organic solvent.

* * * * *